United States Patent [19]
Klein et al.

[11] Patent Number: 5,724,032
[45] Date of Patent: Mar. 3, 1998

[54] METHOD AND APPARATUS FOR COMPRESSING AND DISPLAYING DIGITAL DATA, PARTICULARLY THE HEART RATE OF FETAL MONITORS

[75] Inventors: Ralf Klein, Boeblingen; Herbert Secker, Stuttgart, both of Germany

[73] Assignee: Hewlett-Packard Company, Palo Alto, Calif.

[21] Appl. No.: 660,637

[22] Filed: Jun. 7, 1996

[30] Foreign Application Priority Data

Jul. 1, 1995 [DE] Germany ............. 195 24 092.8

[51] Int. Cl.$^6$ .................. G06F 19/00; A61B 5/0444; H03M 7/30
[52] U.S. Cl. ................... 341/50; 128/698; 345/134
[58] Field of Search .............. 341/50, 51; 128/682.04, 128/698; 345/134, 132

[56] References Cited

U.S. PATENT DOCUMENTS

| | | | |
|---|---|---|---|
| 4,499,548 | 2/1985 | Beebe | 364/575 |
| 4,634,970 | 1/1987 | Payne et al. | 324/121 R |
| 4,754,205 | 6/1988 | Diller et al. | 315/377 |
| 4,920,489 | 4/1990 | Hubelbank et al. | 364/413.6 |
| 5,123,420 | 6/1992 | Paret | 128/698 |
| 5,266,938 | 11/1993 | Mogi | 345/204 |

FOREIGN PATENT DOCUMENTS

3827808A1  8/1988  Germany.

OTHER PUBLICATIONS

IBM Technical Disclosure Bulletin, vol. 30, No. 12, May 1988.

*Primary Examiner*—Brian K. Young
*Assistant Examiner*—Peguy JeanPierre

[57] ABSTRACT

A method and an apparatus for compressing and displaying digital data, in particular beat-to-beat heart rate data in fetal monitoring, operates according to the principle of the "maximum absolute differences", i.e., the data discovered in a certain interval are compared with a start value, and the data with the highest absolute difference in relation to said start value is chosen as representative for the data discovered in such interval. This results in an effective data compression, without suppressing higher-frequency signal components—which are very important for certain applications—significantly.

14 Claims, 7 Drawing Sheets

METHOD AND APPARATUS FOR COMPRESSING AND DISPLAYING DIGITAL DATA, PARTICULARLY THE HEART RATE OF FETAL MONITORS

FIELD OF THE INVENTION

The present invention relates to a method and an apparatus for data compression or data filtering, which are useful especially for applications in which a large quantity of high-resolution digital data is to be represented on a monitor, or alternatively on a printer or another output device, which has a lower resolution than the data. In a special, particularly advantageous application, the invention relates to the representation of a child's heart rate calculated from beat to beat on a monitor in fetal monitoring.

BACKGROUND OF THE INVENTION

The problem on which the present invention is based will be explained for reasons of simplicity with reference to a concrete example: it was in this context that the invention was in fact developed. However, this in no way signifies that the applicability of the invention is restricted to this concrete example; in fact the following discussion will show that the invention can also be employed successfully in other, completely different applications.

So-called fetal monitoring (or cardiotocography) is concerned with registering data relevant to the clinical assessment of the condition of a fetus before or during birth. Typically, the child's heart beat and the uterine contraction activity of the mother are registered, recorded, and reproduced on a printer. During pregnancy, biological signals are picked up from the abdominal wall of the expecting mother by means of non-invasive sensors, e.g. by a uterine contraction sensor with resistance measuring bridges and an ultrasound sensor whose ultrasound beam is directed at the fetal heart; the motion of the heart walls and heart valves then causes a Doppler shift in the reflected beam which can be measured and used to determine the child's heart rate. After rupture of the membranes, on the other hand, i.e. immediately before and during birth, direct measuring techniques are used, for example a pressure sensor introduced into the vagina for determining uterine contraction activity, and a spiral electrode which is screwed into the fetal scalp and which allows direct sensing of the electrocardiogram.

The decisive clinical information this method of measurement is able to provide is not only derived from the curves for the child's heart rate and the mother's uterine contraction activity. Rather, it is the mutual relationship between the two curves which is of primary significance. For example, a deceleration in the fetal heart rate channel, i.e. a temporary drop in the heart rate, can lead to different diagnoses depending on whether the deceleration takes place simultaneously with a uterine contraction or is shifted on the time axis relative to it. Clinical assessment of the relationship between the two curves is complex and has already been the subject of many clinical treatises and studies; see for instance the series of articles entitled "Einführung in die Cardiotokographie" (Introduction to Cardiotocography) by Prof. K. Hammacher in issues May 1976 to August 1977 of the journal "Die Schweizer Hebamme" (The Swiss Midwife). The assessment of the cardiotocogram described there has become part of the standard curriculum in the training of midwives. Successful attempts have also already been made to make the basic rules of cardiotocogram assessment available in an automated form, i.e. with the help of an expert system; see for instance PCT publication WO 93/08534.

Two (interrelated) aspects of cardiotocography deserve to be emphasized. Firstly, midwives and doctors are in fact less interested in the fetal heart rate itself. Rather, the fetal heart rate is an indirect parameter, since the quantity which is in fact relevant is the oxygen supply to the fetus. (For example, a compression of the umbilical cord due to a uterine contraction which causes a lack of oxygen to the fetus, manifests itself in a strong deceleration, since the fetal heart can no longer transport enough blood and so beats more slowly.)

This in turn means that it is not the long- or medium-term values for the child's heart rate which are significant, but primarily the extremely short-term changes. For this reason the fetal heart rate is not determined over a long period of time, but in the shortest possible time interval, namely from heartbeat to heartbeat. In other words, after each heartbeat of the child the instantaneous heart rate is calculated as the inverse of the last interval between heartbeats:

$$HR_{inst} = \frac{1}{T_n - T_{n-1}} \quad (1)$$

where $T_n$ is the time a heartbeat occurs, $T_{n-1}$ the time the previous heartbeat occurred and $HR_{inst}$ the instantaneous heart rate. The instantaneous heart rate calculated from beat to beat is usually known in practice as the "beat-to-beat" heart rate.

For the clinician, it is the short-term changes reflected in the beat-to-beat heart rate which are of primary significance, since they reflect natural physiological irregularities. For example, a heart rate which is constant over a longer period of time, a so-called "silent" heart rate, leads to a pathological diagnosis. For this reason, special terms for short-term heart rate changes have even become established in clinical practice: terms such as "variability", "fluctuations" or "oscillations". In technical terms they signify the higher-frequency components of the signals of the heart rate curve.

Fetal monitors in common use today normally employ a printer (such as a thermal printer) to record the cardiotocogram: for this reason cardiotocographs are sometimes known colloquially as "labor printers". In this recording method the write head moves every time the heart rate changes, so that even the short-term or high-frequency changes are reproduced reliably. In this case the necessary high resolution follows on the one hand from the analog recording method but on the other hand—and primarily—from the fact that the paper strip used for recording is in principle infinite in length. If the paper feed is fast enough it is therefore always possible to achieve a resolution sufficient even for the higher-frequency components of signals.

However, the situation is different if the cardiotocography (CTG) curves are to be displayed on a raster display (screen). A representation of this kind may be necessary for example if the CTG curves are transmitted to a central station, i.e. to monitoring equipment located in the midwife's or doctor's office, used to monitor the data from several delivery rooms. In this case it is impractical to document the data of 8, 12 or even more births on printers, because among other things the fetal monitors located in the various delivery rooms are producing a trace anyway and this would only be duplicated in the monitoring room. Apart from that, it would no longer be possible to survey such a large number of traces in the central station with enough ease to ensure effective monitoring. Therefore the practice of depicting the CTG curves in the central station on a monitor was adopted quite some time ago, allowing the monitoring doctor or a midwife to see the progress of the births and possible complications in the different delivery rooms at a glance.

In addition to this, further applications are conceivable in which displaying CTG curves on a monitor would seem desirable. For instance it would be possible in the long term to abandon the printing technique employed heretofore and to depict the results of measurements on a screen right beside the bed of the pregnant woman as well, in which case, of course, it would also be necessary, for reasons of liability, to archive the data electronically as well.

However, all these solutions have a decided disadvantage, namely the limited resolution of a raster display. The resolution of the uterine contraction curve is not critical here, and the amplitude of the heart rate curve can be represented on all common monitors without any difficulty (the heart rate of a fetus can reach a value of 240 bpm—beats per minute—at most, and practically all commercial monitors offer this resolution in the y-axis direction. In Europe, the maximum fetal heart rate to be registered has in fact been limited to a value of 210 bpm.).

The resolution of the heart rate curve in the direction of the time coordinate i.e. in the direction of the x- or t-axis is, however, critical. If it is assumed that the heart rate is represented with a resolution of 250 ms (milliseconds) in time—this is equivalent to the maximum heart rate of 240 bpm mentioned above—and that the visible trace window is to span a period of 30 minutes, we obtain 4×60×30=7200 data values to be represented in the x direction. Within the limits of acceptable costs this number far exceeds the resolution of commercial monitors such as PC monitors. A typical 38.1 cm (15 inch) PC monitor currently provides a resolution of 1024×768 pixels; this resolution can be expected to be improved to a value of 1280×1024 pixels in the near future. Neither value—1024 or 1280 pixels in the × direction—is sufficient, however, to display the 7200 data values required; and the necessity arises for compressing the data in the ratio of 1:7.03 (for 1024-pixel resolution in the × direction) or 1:5.63 (for 1280-pixel resolution in the × direction).

In the past this problem has been solved by appropriate averaging. However, this leads to the loss of a significant portion of information about the higher-frequency components of the signals; it is easy to see that a sequence of values of 130, 135 and 135 bpm, for example, generates the same average as a sequence of values of 120, 200 and 80 bpm, although the first curve is almost silent, whereas the second represents extreme variability. It is obvious that such a loss of data is hardly tolerable in a clinical application, particularly in view of the significance of the higher-frequency components of the heart rate curve, as discussed above.

Naturally, one possibility would be to narrow the visible time window, in which case 4 minutes and 16 seconds could be displayed on a 1024×768-pixel monitor using its full resolution. However, this time window is not by any means large enough to allow a reliable clinical assessment to be made. In fact the standardized clinical CTG assessment methods, the so-called CTG scoring, are based on the assessment of a 30-minute trace.

Other common methods for data filtering are equally unusable. High-pass filtering might be conceivable; but the DC component (the so-called baseline) of the heart rate curve and other low-frequency components which are also relevant from a clinical point of view would then be lost. In addition, high-pass filtering would not at all achieve the data reduction required.

DE 38 27 808 A1 describes various methods of data reduction for ECG curves, although for the purpose of reducing memory requirements, i.e. not for a raster representation of curves. The calculation of absolute differences provided there is for determining whether a higher resolution is necessary, and not for data reduction itself.

There is thus an urgent need for a data reduction or data filtering method which on the one hand retains the essential information contained in the data—especially in the higher-frequency region—while on the other hand allows the data to be shown on normal commercial raster display screens. This also applies to the need for a corresponding apparatus. It is obvious that a method and an apparatus of this type are also suitable for other applications in which a large amount of data needs to be displayed optically without the loss of essential information, for instance for displaying discrete Fourier spectra or time functions on a digital oscillograph. The solution of these problems is the subject of the present invention.

BRIEF DESCRIPTION OF THE INVENTION

One aspect of the present invention is related to a method for compressing digital data for a raster representation with at least two dimensions on a digital computer, where, at least in the direction of abscissa, the raster resolution is smaller than the resolution of the digital data itself. This method is characterized by the following steps:

1. Selecting an ordinate value for the first raster point to be displayed,
2. Starting a counter for the abscissa values of the raster points,
3. Determining the maximum absolute difference between the ordinate values of the data in an interval defined by a compression factor $c_i$ and beginning at or after the abscissa value of the last raster point determined, and the ordinate value of the last raster point,
   3.1 wherein the compression factor $c_i$ is calculated from the formula $c_i = D_i / P_i$ where $D_i$=the total number of data items to be displayed in the abscissa direction and $P_i$=the number of raster points available for displaying in the abscissa direction,
4. Selecting the ordinate value of that raster point which corresponds to the maximum absolute difference determined in step 3 as the ordinate value of a new raster point,
5. Incrementing the counter, and
6. Repeating the steps of the method beginning with step 3, until the ordinates of the desired number of raster points have been determined.

In the following, for reasons of simplicity, it will be assumed that the data is two-dimensional data with the time axis as the abscissa and the amplitude value as the ordinate, and that the data has to be compressed, along the time axis. This limitation, which is reasonable for description purposes, does not however in any way imply that the invention is limited to this type of situation. In fact the abscissa does not have to represent time-dependency. Abscissa and ordinate can be interchanged and/or so displayed and the method can even be applied to data with more dimensions.

According to the method of the invention, in a first step an ordinate value for the first raster point to be displayed is selected. ("Raster point to be displayed" is understood to mean here the first point in the raster representation, with the lowest abscissa value.) The ordinate value of this point can either be selected arbitrarily or according to certain rules, e.g. according to the ordinate value of the first data item or in dependence of the data history, if available). The first raster point is thus characterized by the lowest-value abscissa to be displayed and by the ordinate selected according to the step described here.

Next a counter representing the abscissa values of the raster points is started. Depending on the representation desired the initial value of this counter can in principle be any value at all: this is only a question of convention. Predominantly an initial value of 0 or 1 will be used; however, if for example a screen display is desired which starts not at the left edge of the screen, but rather at the raster point with the abscissa 200, the counter will also, conveniently, be set to the initial value 200. In principle the counter increment is also arbitrary, although the value 1 will usually be selected.

For the next step—labeled number 3 above—it is necessary to know a compression or data reduction factor, which is characterized here by the constant $c_i$. This compression factor is determined by the ratio between the number of data items to be represented, $D_i$, and the number of raster points, $P_i$, actually physically available along the time axis according to the formula $$c_i = \frac{D_i}{P_i} \tag{2}$$

This value does not of course have to be calculated anew for each approximation step of the filtering method of the invention. Rather, it can already be calculated and defined as a constant when the compression method is programmed. It is, however, more advantageous to calculate this value only upon execution of the program, because different values of $P_i$ can then be taken into account depending on the physical conditions; in other words, the method can then adapt itself to output devices with different resolutions and thus be device-independent. Even in this latter case it is, however, not necessary to calculate the value of $c_i$ for each calculation; it is rather sufficient if this is done once at the beginning of the process. A value for $c_i$ once determined can then be retained for the rest of the process.

Using the compression factor $c_i$ it is then possible to evaluate a certain number of data values in an interval defined by the last raster point evaluated and by the compression factor. For example, let us assume that the first raster point is defined by the abscissa and the ordinate 0, and that the compression factor $c_i$ is 5. Then the data with indices 1–5 will be evaluated.

With reference to the data being evaluated a method of ascertaining the difference in comparison to the last raster point determined (defined or calculated) is employed, i.e. the difference between the ordinate of each of the data items being evaluated and the ordinate value of the last raster point determined is ascertained. The absolute value of each of these differences is obtained. In symbols, this operation can be described as follows:

$$\Delta = |\delta(i) - R| \Big|_{i=1}^{i=c_i} \tag{3}$$

where $\Delta$ is the difference in each case, $\delta(i)$ the data in the interval being evaluated and R the last raster point determined.

The point of this method lies in obtaining that data value in the interval being evaluated whose ordinate depicts the largest absolute distance from the last raster point determined. The ordinate value of this data item with maximum absolute ordinate difference from the last raster point determined is now used as the ordinate value of the next raster point. Next the counter is incremented and the method begins again from step 3 (i.e. the last raster point determined each time is compared with the data of the interval being evaluated). This method is continued until the desired number of raster points has been calculated.

It is obvious that with this compression method a considerable reduction in the number of digital values to be displayed is possible, and in particular, it is possible to adapt the amount of data to the resolution of discrete output devices, primarily display screens. Moreover, if the compression factor $c_i$ is not programmed as a constant, but calculated during the compression method itself, the method can adapt itself to any output device whatsoever, and can do this independently of its actual resolution. Thus, a truly device-independent data reduction method is obtained.

What is much more important in practice, though, is that it has been shown that the compression method of the invention essentially retains the higher-frequency components of the original signal. Naturally, the information content of the filtered signal can no longer correspond exactly to that of the original signal, but for a visual assessment—which by nature cannot take all the subtleties of a complex signal into account—the curve still contains all relevant frequency components. It is precisely this which is a decisive factor in an application such as the assessment by a clinician of a child's heart rate curve in cardiotocography, because what is diagnostically significant about the variability of the signal under scrutiny is not suppressed. On the contrary, the "compression method of maximum absolute differences", as the method of the invention might also be called, due to its preferential treatment of large jumps in the signal, places emphasis on precisely the higher-frequency components and is thus far superior to the averaging methods employed to date. On the other hand, the functionality of the new method is not comparable to a high pass, either, since the low-frequency and DC components of the original signal are by no means suppressed—and this, too, as shown here, is an important characteristic from a clinical point of view, since the baseline fluctuations also contain valuable diagnostic information. Moreover, it is immediately apparent that the compression method of the invention is very fast, i.e. only demands a very small amount of additional computing time, as it is based solely on the basic rules of arithmetic and does not require any complicated mathematical operations such as Fourier transformations or convolutions. Thus it is also suitable for all other applications requiring data reduction without significant suppression of higher-frequency components, such as for example displaying rapid build-up transients on a digital oscillographic screen, but also on a printer with a resolution based on bit patterns, and other such devices.

From a technical viewpoint it could be argued that in fact two counters are required for conducting the method, namely a first counter to count up the raster points and a second counter which points in each case to the first data value in an interval being evaluated. However, this is only partly true. It is of course possible to work with two counters of this kind, but since the values of the two counters are interdependent, it is sufficient to increment only one counter and to calculate the current value of the second "counter" from the first each time. (An example illustrates this clearly: with a compression factor $c_i=3$, for instance, the raster point counter is incremented by 1 from cycle to cycle, while the data counter must be incremented by 3. I.e.

$$C_D = 1 + 3(C_R - 1) \tag{4}$$

where $C_R$ is the value of the raster point counter and $C_D$ the value of the data counter.)

Thus, in practice, a single counter is sufficient. It is therefore also a simple matter to count the data values instead of the raster points, because the last value is an indirect measure of the abscissa of the raster points. It is clear that the term "counter for the abscissa values of the raster points" in the scope of the invention thus also covers a counter for the data values, since the latter naturally also contains the raster point counter.

In the description so far it has been assumed that the compression factor $c_i$ takes on an integer value. However, this assumption must be dropped to obtain a truly device-independent compression method, since a fractional value for $c_i$ may of course also arise. According to an advantageous enhancement of the invention, this situation is dealt with in the following manner:

The set $D_i$ of the ordinate values of the data evaluated per interpolation interval (i.e. included in the determination of the differences) is calculated to be $$\{D_i\}=INT(kc_i)-INT((k-1)c_i) \qquad (5)$$

where k is a sequential number and INT defines the integer function. In other words, if the compression factor $c_i$ consists of an integer and a fractional component, only the integer component is considered for the first interval evaluated, and perhaps for other intervals as well. The fractional remainders are added together and as soon as this total exceeds 1, the interval is increased by 1, in order to take the cumulated remainders into consideration. So for instance, if we take a compression factor of $c_i=6.4$, the first two intervals will each include six data items. On evaluation of the third interval, the cumulated remainders have reached a value of 1.2, so 7 data values must be included in the third interval (and in addition, a remainder of 0.2 for determining future intervals must be taken into consideration).

There are several advantageous alternatives for starting the method of the invention. For instance, a constant value can be assumed for the ordinate value of the first raster point to be displayed, or the ordinate of the first digital data item can be selected. However, the matter becomes critical if no valid data is available for a time; this may especially apply in case of clinical applications. If data items are only missing within an interval or in the amount of at most one interval, they can simply be ignored without much loss of accuracy. But if data items are missing from more than one interval or in the amount of more than one interval, the method comes to a temporary standstill. When this occurs it is advantageous not only to ignore the missing data, but also to select a new raster point for a fresh start of the method when data again becomes available. It is preferable then to select a new raster point whose ordinate corresponds to the ordinate of the first valid data item which becomes available.

The invention also relates to a method of filtering and displaying digital data on an output device based on the raster principle, preferably a raster display or a printer whose raster resolution in at least one coordinate direction is less than the resolution of the digital data itself, and the method is characterized by the following steps:

1. Selecting an ordinate value for the first raster point to be displayed,
2. Starting a counter for the abscissa values of the raster points or for the digital data,
3. Determining the maximum absolute difference between the ordinate values of the data in an interval defined by a compression factor $c_i$ and beginning at or after the abscissa value of the last raster point determined, and the ordinate value of the last raster point,
   3.1 wherein the compression factor $c_i$ is calculated from the formula $c_i=D_i/P_i$ where $D_i=$the total number of data items to be displayed in the abscissa direction and $P_i=$the number of raster points available for displaying in the abscissa direction,
4. Selecting the ordinate value of that raster point which corresponds to the maximum absolute difference determined in step 3,
5. Incrementing the counter,
6. Repeating the steps of the method beginning with step 3, until the ordinates of the desired number of raster points have been determined,
7. Transferring the coordinates of the raster points calculated to the output device, and
8. Reproducing the raster point calculated on this output device.

The data can naturally be transferred to the output device either in steps—i.e. each raster point is transferred to the output device immediately on its being determined or calculated—, or the coordinates of the raster points determined or calculated are first collected in the computer and then transferred to the output device block by block.

The invention also relates to an apparatus for compressing or filtering digital data for a raster representation with at least two dimensions on a digital computer, wherein the raster resolution is less than the resolution of the digital data itself at least in the direction of the abscissa, particularly an apparatus for determining and/or displaying fetal monitoring data, where the apparatus includes at least the following components:

- a processor, preferably a microcomputer, for conducting the compression or filtering process;
- a data processor or data memory for providing data, in particular the heart rate of a fetus;
- a counter for the abscissa values of the raster points or for the digital data;
- a difference-determining facility for determining the maximum absolute difference between the ordinate values of the data in an interval defined by a compression factor $c_i$ and beginning at or after the abscissa value of the last raster point determined, and the ordinate value of the last raster point; and
- a selection apparatus for selecting the ordinate of that raster point which corresponds to the maximum absolute difference determined in the previous step as the ordinate value of a new raster point.

In an advantageous enhancement this apparatus also comprises a digital output device, preferably a raster display, on which the raster points determined are displayed. If a division facility is provided for determining the compression factor $c_i$ according to the formula $$c_i=D_i/P_i$$

(where $D_i=$the total number of data items to be displayed in the abscissa direction and $P_i=$the number of raster points available for displaying in the abscissa direction), then an apparatus is obtained which is independent of the output device being used and can adapt itself to any output device whatsoever.

BRIEF DESCRIPTION OF THE FIGURES

The invention will now be explained in more detail using a preferred embodiment, with reference to the accompanying figures, which depict the following.

DETAILED DESCRIPTION OF THE PREFERRED EMBODIMENTS

Figure 1:
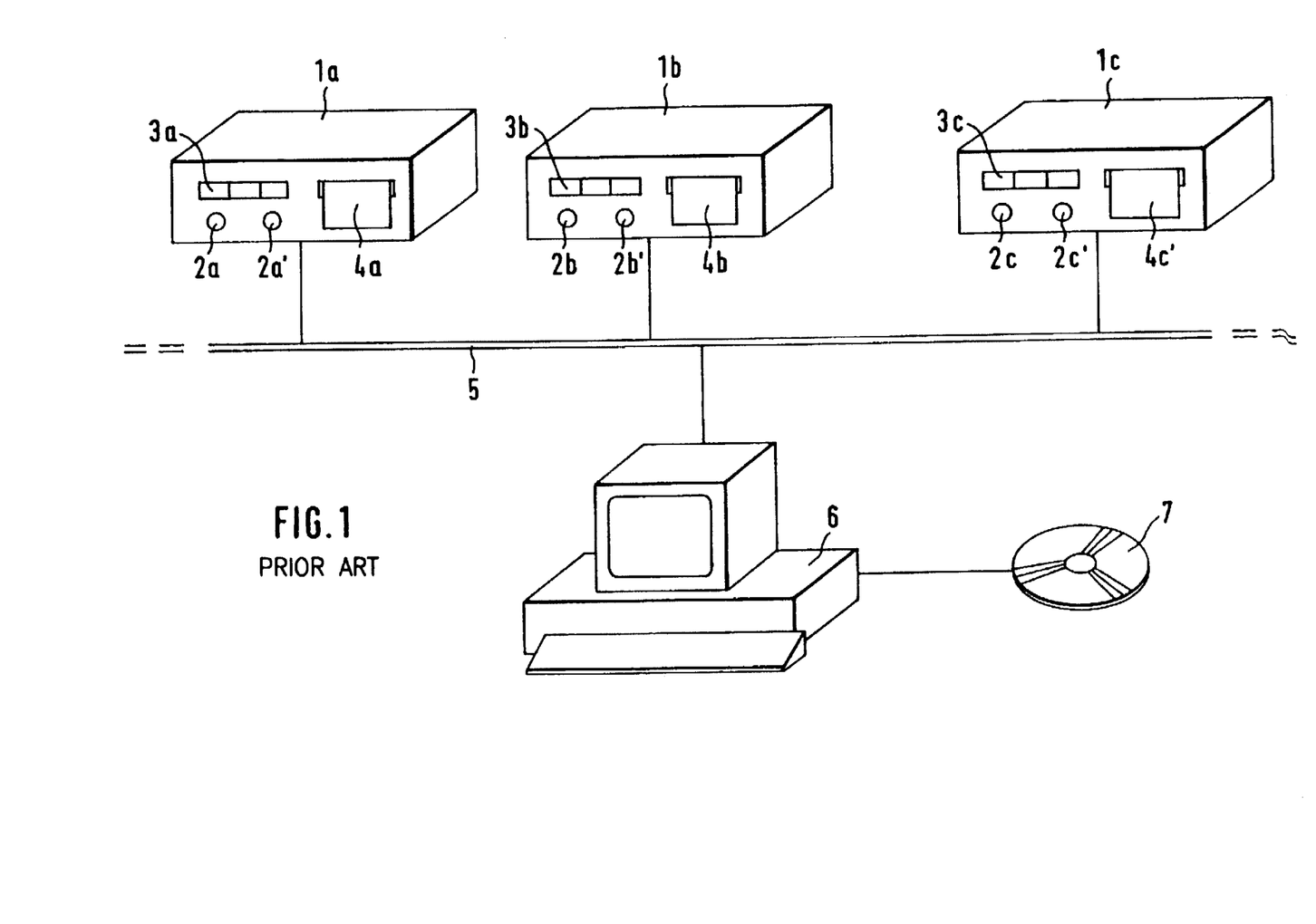
FIG. 1 simple system of networking fetal monitors with a central station.

FIG. 1 shows a typical clinical environment for monitoring and recording cardiotocographic data as it may be found in medium-sized hospitals, for example. Fetal monitors 1a to 1c of a common type, as described for instance in U.S. Pat. No. 5,123,420, are located in several delivery rooms. These fetal monitors comprise at least one channel for the heart rate and one for uterine contractions, and may also have a second heart rate channel for monitoring twins and/or a channel for monitoring fetal oxygen saturation. In FIG. 1, however, only two connectors $2a$, $2a'$ to $2c$, $2c'$ are shown for the corresponding sensors of each unit.

The results of the measurements are shown on the built-in displays 3a to 3c. This instantaneous display is only of secondary importance, however; what is essential for the diagnostic assessment of the fetal condition is the assessment of an at least 30-minute trace of both the fetal heart rate and the uterine contraction activity of the mother. For this reason there is a printer 4a to 4c—a thermal printer, for example—built into each of the fetal monitors 1a to 1c on which these curves are plotted. One example of a trace of this type will be discussed with reference to FIG. 2, later.

Fetal monitors 1a to 1c are each connected to a central data channel 5 which may be a standardized data bus, for example. Devices for further processing of clinical data may be connected to this data channel. FIG. 1 shows as an example a central station, here in the form of a personal computer (PC) 6. This PC can be located in the office of the monitoring doctor and allows him or her to monitor several delivery rooms at once, without the need for a doctor to be present in each of these rooms. If the doctor sees on the screen that one of the imminent births has reached a critical condition, he or she can personally intervene at any time.

It is clear that the combination of devices shown in FIG. 1 merely represents a minimal configuration. In large hospitals there may be several central stations, PCs can be assigned to each of the cardiotocographs, the data can be transferred via telephone modems to distant locations, many more than three beds can be monitored by a single central station, etc. In addition, a central data storage point will be provided in a large hospital for archiving patient data for liability purposes. (FIG. 1 shows the symbol of an optical disk 7 connected to PC 6 for this purpose.)

However, the difference between larger and smaller networks is not relevant to the objective underlying the present invention. Rather, the essential point is that it is not practical to duplicate in the central station the traces made by the fetal monitors in each of the delivery rooms. To do this would not only be uneconomical, but would also be a source of confusion to the monitoring doctor, because given a typical number of 8 beds to be monitored, he or she would spend more time sorting out the multitude of paper strips than actually getting down to interpreting them.

The use of screen displays in the central station is thus unavoidable. But it is here that the problem of the limited resolution of the raster display screens currently in use, which lies on the order of 1024×768 pixels, is encountered. However, as the fetal heart rate curve has a resolution of 250 milliseconds (corresponding to a maximum heart rate of 240 bpm), 7200 raster points are needed for a 30-minute trace fulfilling clinical requirements.

Figure 2:
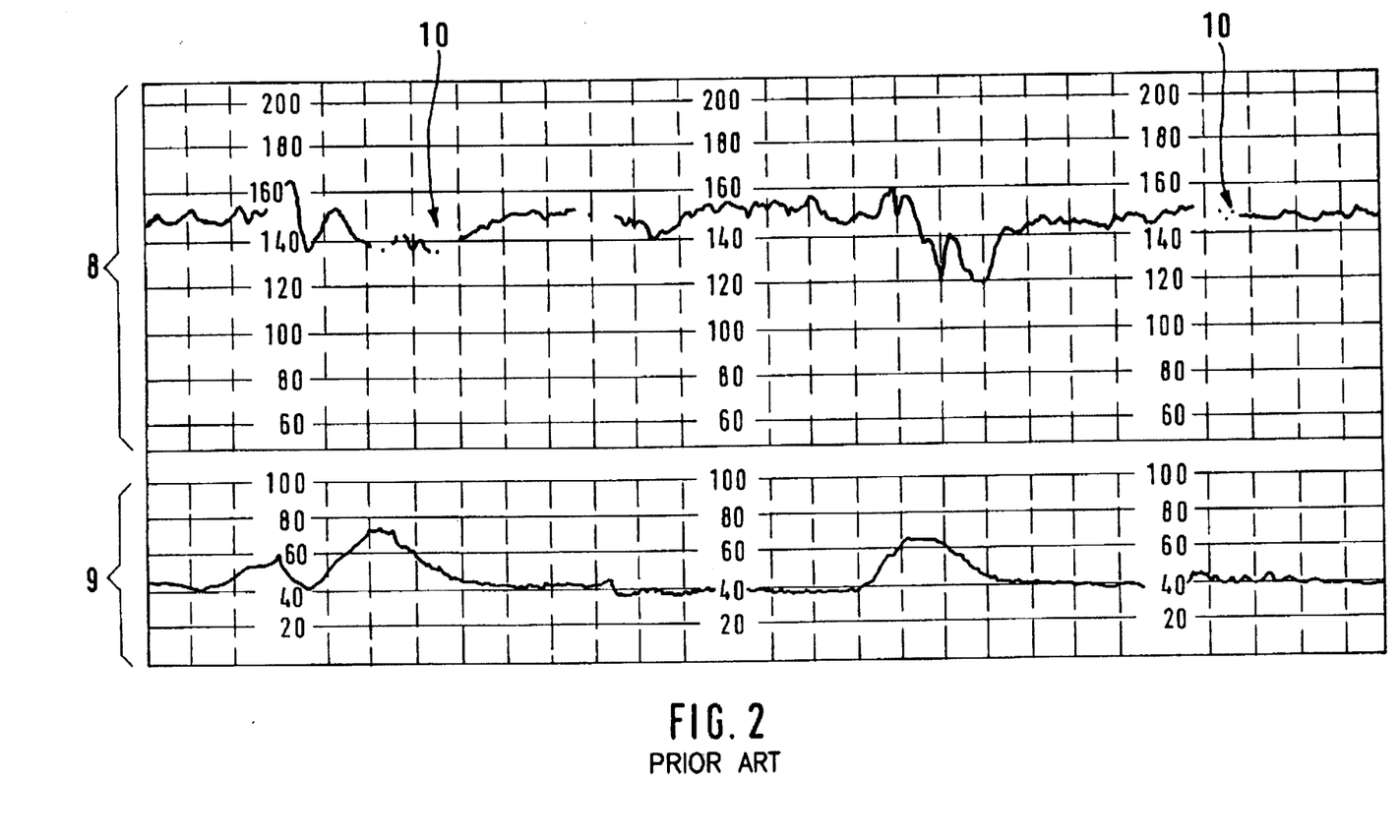
FIG. 2 an example of a typical cardiotocogram trace.

Simple averaging to reduce the data provides unsatisfying results, since the fetal heart rate curve contains higher-frequency components which are significant for clinical diagnosis. This is apparent in FIG. 2, which shows a typical cardiotocogram. Here, the heart rate curve is represented by reference symbol 8, and the mother's uterine contraction curve (TOCO) is represented by reference symbol 9. It is clear to see that the fetal heart rate calculated from beat to beat displays short-term fluctuations—mostly from beat to beat—which are relevant for the clinician to recognize. In addition, FIG. 2 shows a further problem frequently encountered in practice, namely signal gaps 10 (caused for instance by an ultrasound sensor not properly focused on the fetal head), which have to be taken into consideration and which can cause signal distortion if averaging is employed.

Figure 3:
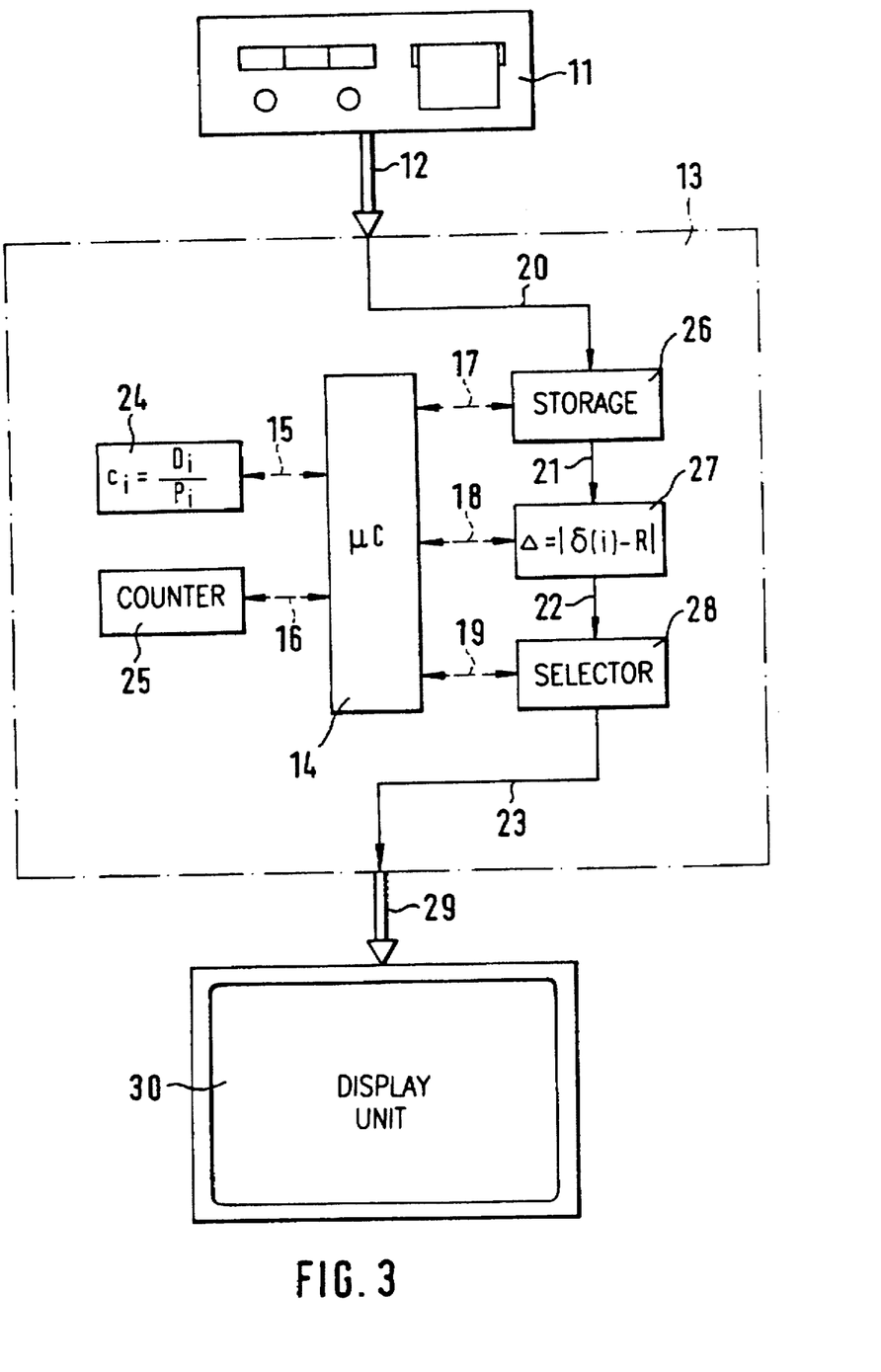
FIG. 3 the block diagram of an embodiment of the compression and filtering apparatus according to the present invention FIGS. 4a and 4b an example of a flow diagram illustrating the operating method of the invention FIG. 5 a graphical depiction of how compressed raster points are determined from original data, and FIGS. 6 and 7 graphical illustrations similar to FIG. 5 showing how the method of the invention works when original data are temporarily missing.

One configuration in accordance with the present invention, which achieves data compression almost completely without the loss of the higher-frequency signal components and which is thus particularly suitable for compressing heart rate data, is shown in FIG. 3. The heart rate data of a fetal monitor 11 (and perhaps other data produced by it, such as the mother's uterine contraction measurements) is transmitted via a data line 12 to a digital computer 13. This digital computer can be a personal computer, although it does not have to be one. It is represented in FIG. 3 as a block outline consisting of dots and dashes, to distinguish it from the function blocks which are most important to the present invention.

Within the digital computer 13 a microcontroller 14, for example a microprocessor of Intel, Inc., controls the essential pads of the program. Its control structures are indicated by dashed lines 15–19. The main flow of the heart rate data is indicated by the continuous-line arrows 20–23.

As auxiliary facilities the microcontroller 14 primarily comprises a division facility 24 for determining the compression factor $c_i = D_i/P_i$, and a counter 25. These facilities—as well as other function blocks of digital computer 13—may be realized either as hardware components (for instance in the form of a floating-point processor in the case of division facility 24 and a discrete counter 25) or as software functions.

The actual processing, i.e. compression and filtering, of the heart rate data coming in via data line 12 is carried out in function blocks 26–28. The data processor or data storage facility 26 receives the heart ate data and the difference-determining facility 27 determines the maximum absolute difference of the ordinate values of the data lying in an interval defined by a compression factor $c_i$ and beginning at or after the abscissa value of the last aster point determined, and the ordinate value of the last raster point. A selection apparatus 28 then selects the maximum absolute difference as the ordinate value of a new raster point, which is then transmitted via a data line 29 to be displayed on a raster display 30.

Figure 4A:
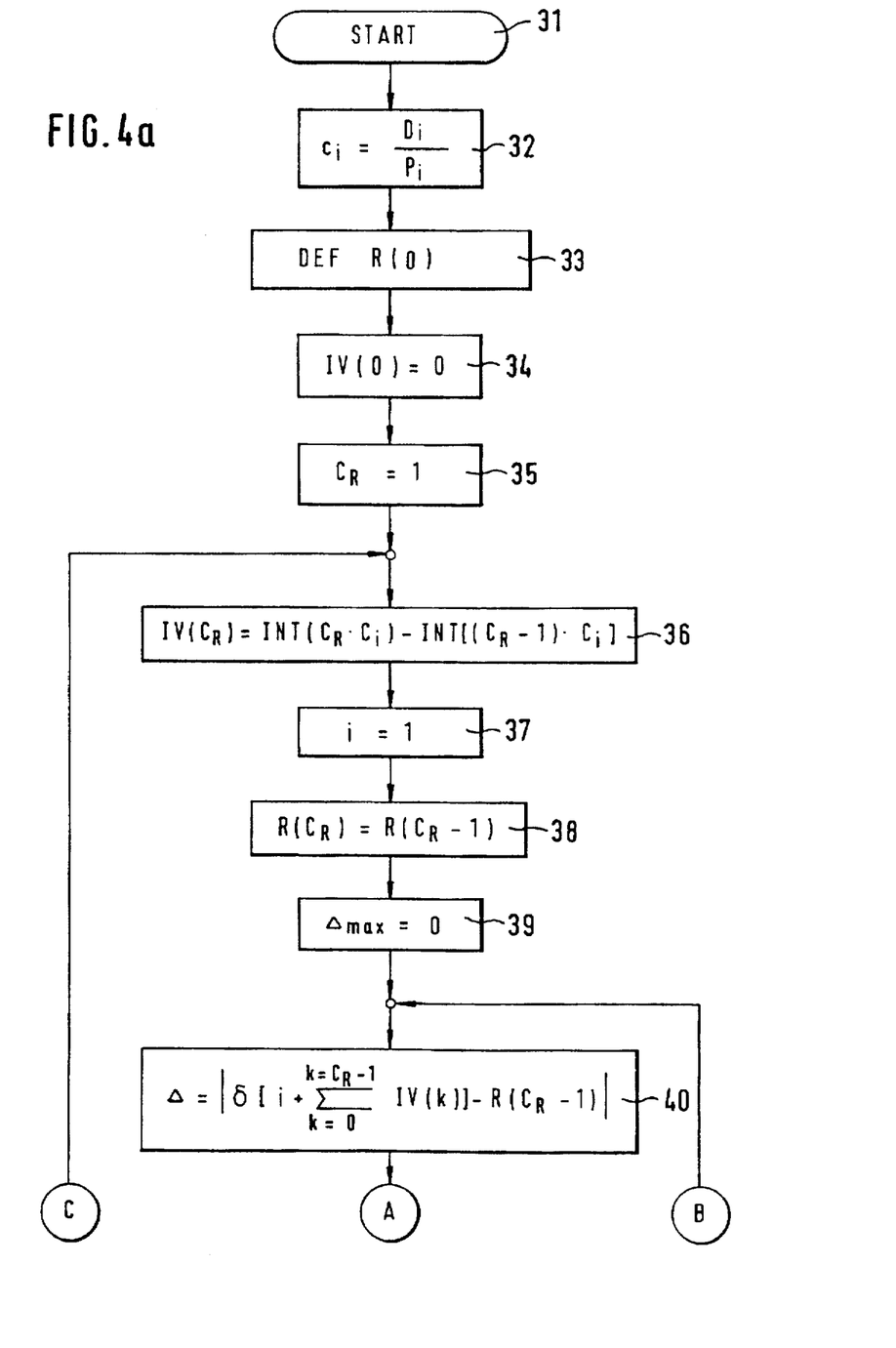
Figure 4B:
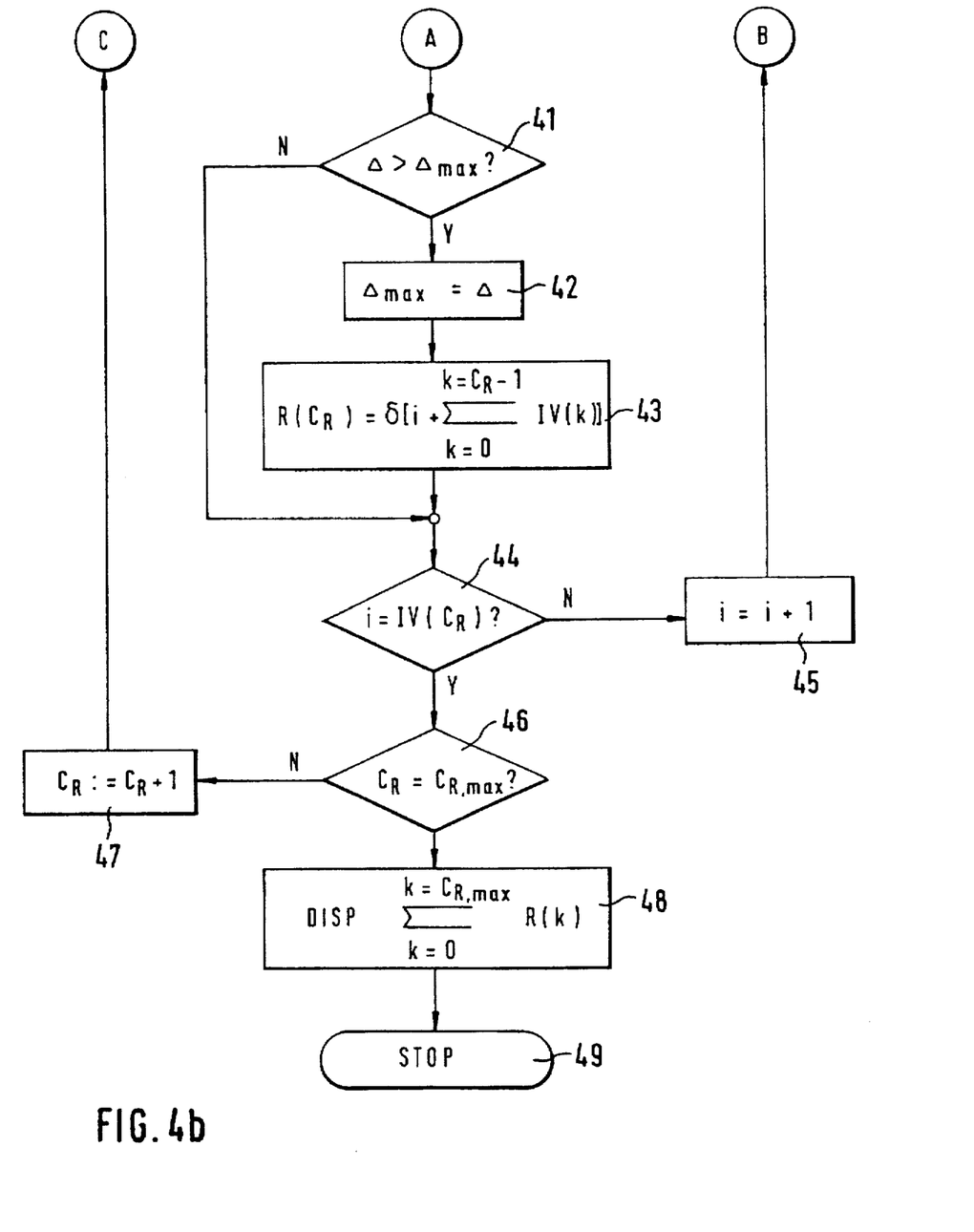

With reference to the connected flow charts of FIGS. 4a and 4b, the operating method of the invention will now be illustrated in more detail. After the start (reference symbol 31) in FIG. 4a, the compression factor $c_i$ required is first calculated (block 32) from the ratio of the total number of data items $D_i$ to be displayed, e.g. 7200 in relation, to the number of raster points $P_i$ available, e.g. 1125. In this case this leads to a compression ratio of $c_i = 6.4$. In accordance with the reference symbol 33 the ordinate of the first raster point R(0) is then defined. This ordinate is selected according to considerations of expediency; for example a typical ordinate value, such as 120 bpm, or the initial value 0 can be selected. Other alternatives are the ordinate of the first data value or an average obtained from the first few data values.

The length of the first interval IV is only set to 0 (step 34) to ensure that the method will work properly, because the later step 40 assumes that an interval with index 0 will be accessed. Thus, step 34 is not fundamentally important to the invention. Next, a raster point counter $C_R$ is set to 1 (step 35). This completes the initialization stage.

Now the processing of the first data interval commences. The length of the interval, i.e. the number of data items included, is calculated according to the formula given in block 36. Then counter i is started—step 37—which counter counts up the data within an interval, from 1 to the length of the interval IV ($C_R$). In block 38 the ordinate value of the raster point to be determined $R(C_R)$ is set to the ordinate value of the previous raster point, beginning with raster point R(1) for the first raster-point counter value $C_R$=1. This is merely a safety measure which guarantees that a reasonable new raster point is defined, even if the ordinates of all data in the interval being evaluated are equal to the previous raster point and thus differences of 0 are obtained across the entire interval.

Then the maximum difference occurring within an interval, $\Delta_{max}$, is set to 0 (step 39). This completes the initialization for a data interval under consideration, and the actual processing of this interval can begin.

For all data items within the interval a difference $\Delta$ is first formed according to the formula given in block 40. Here, quantity $\delta$ represents the data items. Their index is obtained from the number of data items (i) in the interval already processed plus the sum of the data processed in previous intervals. The sum over all intervals IV(k) is thus an indirect counter for the data. As explained earlier, it is of course possible to count the data separately, but due to the interdependence of the counting of the raster points and the counting of the data, this is not necessary.

With reference to all data $\delta$ within an interval, each difference $\Delta$ is determined in comparison to the ordinate of the previously determined raster point $R(C_R-1)$. As the maximum deviation, irrespective whether in a positive or negative direction, is to be determined, the absolute value of this difference is also calculated. Operation now continues, via reference point A, with the diagram of FIG. 4b.

In query 41 it is ascertained whether the calculated difference $\Delta$ is the largest within the interval being evaluated, i.e. whether it exceeds the value $\Delta_{max}$. If this is the case, $\Delta$ is set as the new maximum value for the difference (i.e. $\Delta_{max}$:=$\Delta$, see step 42). In this way the data item $\delta$ with the largest absolute ordinate difference compared to the previous raster point within an interval can be determined.

However, it must be observed that the maximum difference $\Delta_{max}$ is only used to determine the data item with the maximum absolute difference from the last raster point determined, and is not directly used for the raster display. Rather, it is the ordinate of the data item which is used to fix upon a new raster point $R(C_R)$, as described in step 43. This new raster point represents the result of examining an interval, if it is not then replaced by a raster point with a larger $\Delta_{max}$.

In step 44 counter i (within an interval) is checked to see whether it has yet reached its maximum value IV($C_R$). If not, it is incremented by 1 (reference number 45), and the next data item $\delta$ within the interval is examined (return via reference point B to the diagram in FIG. 4a).

However, if the counter i has reached its maximum value, the examination of an interval has been completed, and the current value $R(C_R)$ defines a new raster point. Now step 46 is used to check whether all intervals have been examined yet, i.e. whether $C_R$=$R_{R,max}$. (Quantity $C_{R,max}$ is predefined by the resolution of the output device and is therefore given as $C_{R,max}$=$P_i$-1.) If this is not the case, the raster point counter $C_R$ is incremented (step 47), and operation returns via reference point C to the diagram in FIG. 4a. Otherwise all raster points R(k) required for the display have been determined, and they can be displayed, for example, on a monitor (see function block 48). The method of the invention is now completed (step 49), until it is required and called the next time.

Incidentally, the functionality of the invention can also be illustrated using pseudocode which can have the following sequence:

|STEP A|:

for (i=1 to all device pixels add 1 to i)

do

CurrentPTG=integer(float(PTG i))−integer(float(PTG (i−1)))

for (k=1 to CurrentPTG)

do

|STEP B|

PixelToPaint(PP)=DIFTA(DataPixel)

done done where 'PTG' means 'pixel to group', i.e. the number of raster points to be combined per interval (6.4 in the example above); 'DataPixel' is the abscissa of a raster point; and 'PixelToPaint', or PP, is the ordinate of a raster point to be displayed on an output device.

In step |STEP B|, i.e. the DIFTA function, the following steps must be conducted:

a) initialization of the following variables:

PixelToPaint(PP) to 0;

Difference (Diff) to 0;

Current Difference (CurDiff) to 0;

Starting Point (SP) to the previous output value of the filter, otherwise 0.

b) execution of the following pseudocode:

for (all data pixels to filter (CurrentPTG from |STEP A|))

do

CurrDiff=abs(data pixel−SP)

if (CurDiff>Diff) then do

Diff=CurrDiff

PP=data pixel done done after which the output point PP can be displayed on the output device.

Figure 5:
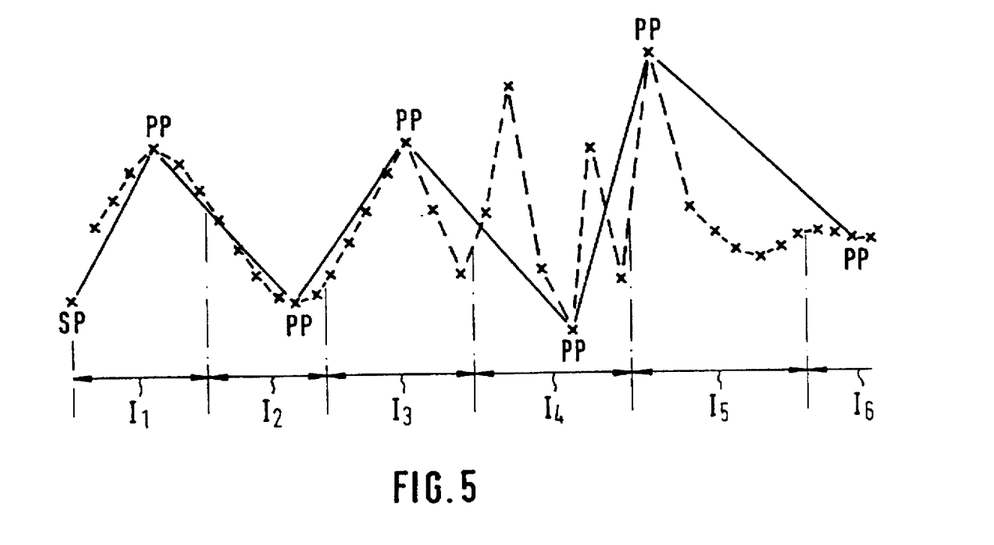

FIG. 5 shows the effect of the compression method on the original data and on the raster points determined. All original data are marked by small crosses; the data intervals examined are labeled as $I_1$, $I_2$, . . . As already explained, these intervals can contain differing numbers of data items if the compression factor $c_i$ has a fractional value. In the case shown where $c_i$=6.4, intervals $I_1$, $I_2$ and $I_4$ each contain 6 data items, whereas there are 7 data items in intervals $I_3$ and $I_5$.

The (more or less arbitrarily selected) initial raster point is labeled as SP=starting point, and all the other raster points determined are labeled as the abbreviation 'PP' (for "PixelToPaint", i.e. raster point to draw). The raster points PP which have been determined are joined by continuous lines; these show the picture to be reproduced on the screen in contrast, the original data are joined together by a dashed line. It is evident that the higher-frequency information is essentially retained, even if the screen image no longer corresponds exactly to the original data. The same applies to the long-term average, i.e. the DC value (or baseline). Note that the raster points PP are by no means always in the middle of, or at the same point in, an interval. This is a consequence of selecting the data point with the maximum absolute deviation from the raster point selected in the previous interval, without taking its abscissa into account.

Figure 6:
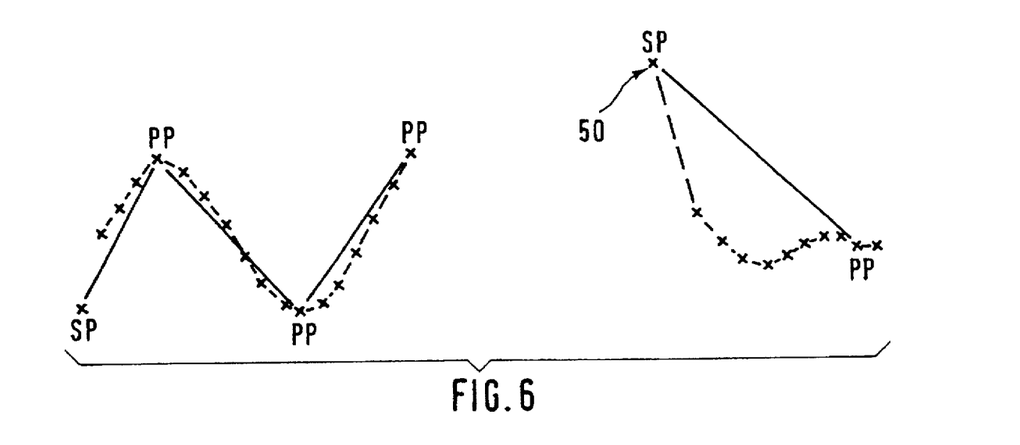
Figure 7:
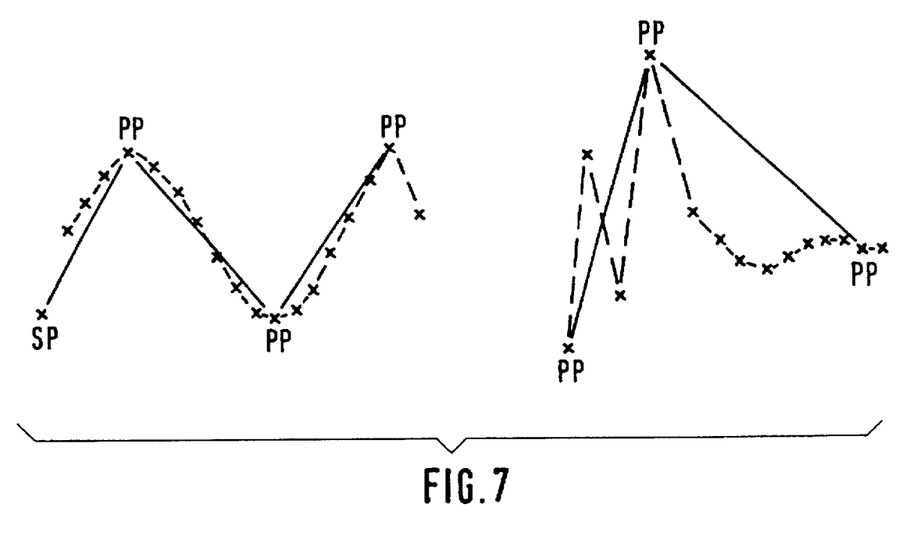

FIGS. 6 and 7 show the complications that arise if single data items are missing—a common problem during fetal heart rate monitoring—and the solution to them. In FIG. 6 data from more than one interval frame are missing. In this case a new starting point (50) must be set, which is here to be equal to the first valid data item that becomes available again. It is clear that the screen image obtained is largely similar to that of FIG. 5 with the exception of the region with the missing data.

In the diagram in FIG. 7, on the other hand, data from less than one interval frame is missing (even though the missing region exceeds an interval boundary). In this case no new starting point is set, but the method is simply continued with the available data. In this case, too, there is no significant deviation from the original raster curve in FIG. 5. (The data in FIGS. 6 and 7 correspond to those in FIG. 5, with the exception of the missing data.)

We claim:

1. Method for compressing digital data for a raster representation with at least two dimensions on a digital computer, where the raster resolution at least in the direction of the abscissa is less than the resolution of the digital data itself, characterized by the following method steps:

(1.1) Selecting an ordinate value for the first raster point to be displayed, (1.2) Starting a counter for the abscissa values of the raster points or for the digital data, (1.3) Determining the maximum absolute difference between the ordinate values of the data in an interval defined by a compression factor $c_i$ and beginning at or after the abscissa value of the last raster point determined, and the ordinate value of the last raster point, (1.3.1) wherein the compression factor $c_i$ is calculated from the formula $c_i = D_i/P_i$ where $D_i$=the total number of data items to be displayed in the abscissa direction and $P_i$=the number of raster points available for displaying in the abscissa direction, (1.4) Selecting the ordinate value of that raster point which corresponds to the maximum absolute difference determined in step (1.3) as the ordinate value of a new raster point, (1.5) Incrementing the counter, and (1.6) Repeating the steps of the method beginning with step (1.3), until the ordinates of the desired number of raster points have been determined.

2. Method according to claim 1, characterized in that the set of ordinate values under consideration is calculated as $$\{D_i\} = INT(kc_i) - INT((k-1)c_i)$$

where k is a sequential number and INT defines the integer function.

3. Method according to claim 1, characterized in that the data are time-dependent physical data.

4. Method according to claim 3, characterized in that the data represents the heart rate of an unborn child or a child being born, calculated from beat to beat.

5. Method according to claim 1, characterized in that a constant value is assumed for the ordinate value of the first raster point to be displayed.

6. Method according to claim 1, characterized in that the ordinate of the first digital data item is assumed for the ordinate value of the first raster point to be displayed.

7. Method according to claim 1, characterized in that upon single missing data items within an interval, or in the amount of not more than an interval, such missing items are not taken into consideration.

8. Method according to claim 1, characterized in that upon missing data exceeding an interval, or in the amount of more than one interval, such missing data items are not taken into consideration, and upon the re-occurrence of valid data, a new raster point is selected for restarting the method.

9. Method according to claim 8, characterized in that the ordinate of the new raster point corresponds to the ordinate of the first re-occurring valid data item.

10. Method according to claim 1, characterized in that the raster points are pixels on a physical output device, preferably a raster display or a printer.

11. Method for compressing and displaying digital data on an output device based on the raster principle, preferably a raster display screen (30) or a printer, whose raster resolution in at least one coordinate direction is less than the resolution of the digital data itself, characterized by the following method steps:

(11.1) Selecting an ordinate value for the first raster point to be displayed, (11.2) Starting a counter for the abscissa values of the raster points or for the digital data, (11.3) Determining the maximum absolute difference between the ordinate values of the data in an interval defined by a compression factor $c_i$ and beginning at or after the abscissa value of the last raster point determined, and the ordinate value of the last raster point, (11.3.1) wherein the compression factor $c_i$ is calculated from the formula $c_i = D_i/P_i$ where $D_i$=the total number of data items to be displayed in the abscissa direction and $P_i$=the number of raster points available for displaying in the abscissa direction, (11.4) Selecting the ordinate value of that raster point which corresponds to the maximum absolute difference determined in step (11.3) as the ordinate value of a new raster point, (11.5) Incrementing the counter, (11.6) Repeating the steps of the method beginning with step (11.3) until the ordinates of the desired number of raster points have been determined, (11.7) Transferring the coordinates of the raster points calculated to the output device, and (11.8) Reproducing the raster points calculated on this output device.

12. Apparatus for filtering digital data for a raster representation with at least two dimensions on a digital computer, wherein at least in the direction of the abscissa the raster resolution is less than the resolution of the digital data itself, particularly an apparatus for determining and/or displaying fetal monitoring data, comprising at least:

(12.1) a processor, preferably a microcomputer, for conducting the filtering process;

(12.2) a data processor or data memory for providing data, in particular the heart rate of a fetus;

(12.3) a counter for the abscissa values of the raster points or for the digital data;

(12.4) a difference-determining facility for determining the maximum absolute difference between the ordinate values of the data in an interval defined by a compression factor $c_i$ and beginning at or after the abscissa value of the last raster point determined, and the ordinate value of the last raster point; and (12.5) a selection apparatus for selecting the ordinate of that raster point which corresponds to the maximum absolute difference determined in step (12.4) as the ordinate value of a new raster point.

13. Apparatus according to claim 12, characterized by a digital output device, preferably a raster display, on which the raster points determined are displayed.

14. Apparatus according to claim 12, characterized by a division facility which determines the compression factor $C_i$ according to the formula $$c_i = D_i/P_i$$

where $D_i$ = the total number of data items to be displayed in the abscissa direction and $P_i$ = the number of raster points available for display in the abscissa direction.

\* \* \* \* \*